US010851336B2

(12) United States Patent
Whitman et al.

(10) Patent No.: US 10,851,336 B2
(45) Date of Patent: Dec. 1, 2020

(54) APPARATUS AND METHODS FOR MAGNETIC MIXING

(71) Applicant: LUMINEX CORPORATION, Austin, TX (US)

(72) Inventors: Doug Whitman, Round Rock, TX (US); James Heisler, Austin, TX (US); Colin Bozarth, Austin, TX (US); Germaine Siew, Austin, TX (US); Charles Collins, Austin, TX (US); Eric Smith, Austin, TX (US)

(73) Assignee: LUMINEX CORPORATION, Austin, TX (US)

( * ) Notice: Subject to any disclaimer, the term of this patent is extended or adjusted under 35 U.S.C. 154(b) by 65 days.

(21) Appl. No.: 16/202,315

(22) Filed: Nov. 28, 2018

(65) Prior Publication Data

US 2019/0093061 A1 Mar. 28, 2019

Related U.S. Application Data

(62) Division of application No. 14/731,459, filed on Jun. 5, 2015, now Pat. No. 10,179,899.

(60) Provisional application No. 62/013,648, filed on Jun. 18, 2014.

(51) Int. Cl.
| | |
|---|---|
| *B01L 7/00* | (2006.01) |
| *C12M 1/06* | (2006.01) |
| *B01F 13/08* | (2006.01) |
| *B01F 13/00* | (2006.01) |
| *B01F 13/10* | (2006.01) |

(52) U.S. Cl.
CPC .......... *C12M 27/02* (2013.01); *B01F 13/0052* (2013.01); *B01F 13/0818* (2013.01); *B01F 13/1022* (2013.01); *B01L 7/52* (2013.01)

(58) Field of Classification Search
CPC . C12M 27/02; B01F 13/0052; B01F 13/0818; B01F 13/1022; B01L 7/52
See application file for complete search history.

(56) References Cited

U.S. PATENT DOCUMENTS

| | | | |
|---|---|---|---|
| 3,088,716 | A | 5/1963 | Stott |
| 4,040,605 | A | 8/1977 | Towsend |
| 4,911,555 | A | 3/1990 | Saffer et al. |
| 5,306,510 | A | 4/1994 | Meltzer |
| 5,352,036 | A | 10/1994 | Haber et al. |
| 5,578,201 | A | 11/1996 | Collier et al. |
| 6,086,831 | A | 7/2000 | Harness et al. |

(Continued)

FOREIGN PATENT DOCUMENTS

| | | |
|---|---|---|
| EP | 1 064 988 | 4/2007 |
| FR | 2 109 370 | 5/1972 |

(Continued)

OTHER PUBLICATIONS

Extended European Search Report and Opinion issued in corresponding European Application No. 15809156.1, dated Jan. 24, 2018.

(Continued)

*Primary Examiner* — Anshu Bhatia
(74) *Attorney, Agent, or Firm* — Parker Highlander PLLC

(57) ABSTRACT

Methods and systems for magnetic mixing. Particular embodiments relate to applying a magnetic field to move a magnetically responsive component in a chamber.

20 Claims, 15 Drawing Sheets

(56) References Cited

U.S. PATENT DOCUMENTS

| | | | |
|---|---|---|---|
| 6,176,609 B1 | 1/2001 | Cleveland et al. | |
| 6,221,584 B1 | 4/2001 | Emrich et al. | |
| 6,357,907 B1 | 3/2002 | Cleveland et al. | |
| 6,461,034 B1 | 10/2002 | Cleveland | |
| 6,579,453 B1 | 6/2003 | Baechler et al. | |
| 7,351,337 B1 | 4/2008 | Milo et al. | |
| 7,484,880 B2 | 2/2009 | Cleveland et al. | |
| 7,791,441 B1 | 9/2010 | Jefferson | |
| 8,657,484 B1 * | 2/2014 | Bottiger | B01F 11/0082 366/273 |
| 10,179,899 B2 | 1/2019 | Whitman et al. | |
| 2002/0154570 A1 | 10/2002 | Gebrian | |
| 2004/0053319 A1 | 3/2004 | McWilliams et al. | |
| 2004/0165474 A1 | 8/2004 | Nesbitt | |
| 2010/0200405 A1 | 8/2010 | Lenz | |
| 2011/0294230 A1 * | 12/2011 | Carron | G01N 21/658 436/525 |
| 2013/0023438 A1 * | 1/2013 | Bachman | B82Y 15/00 506/9 |
| 2014/0004517 A1 | 1/2014 | Nelson et al. | |
| 2014/0134623 A1 | 5/2014 | Hiddessen et al. | |
| 2014/0377764 A1 * | 12/2014 | Stehr | C12Q 1/6844 435/6.12 |

FOREIGN PATENT DOCUMENTS

| | | |
|---|---|---|
| JP | H10-503380 | 3/1998 |
| JP | H11-500015 | 6/2002 |
| WO | WO 1996/017083 | 6/1996 |
| WO | WO 2001/1136 | 2/2001 |

OTHER PUBLICATIONS

International Search Report and Written Opinion, issued in PCT/US2015/034332, dated Nov. 3, 2015.

Invitation to Pay Additional Fees, issued in PCT/US2015/034332, dated Aug. 24, 2015.

Office Communication issued in corresponding Japanese Application No. 2019-035341, dated Jan. 7, 2020.

* cited by examiner

APPARATUS AND METHODS FOR MAGNETIC MIXING

CROSS-REFERENCE TO RELATED APPLICATIONS

This application is a divisional application of U.S. patent application Ser. No. 14/731,459, filed Jun. 5, 2015, which claims priority to U.S. Provisional Patent Application, Ser. No. 62/013,648 filed Jun. 18, 2014, the contents of which are incorporated herein by reference.

FIELD OF THE INVENTION

Embodiments of the present invention relate to mixing components using magnetic fields. Particular embodiments relate to applying a magnetic field to one or more chambers and moving a magnetically responsive component in each chamber to mix contents in the chamber(s).

BACKGROUND

The following descriptions and examples are not admitted to be prior art by virtue of their inclusion within this section.

Chemical and biological reactions, including polymerase chain reactions (PCR), typically utilize multiple types of reagents in one or more physical states. It is often desirable to mix the components of the reaction, for example to increase efficiency and/or consistency of results. Lyophilized reagents, in particular, may require more extensive mixing than liquids in order to rehydrate and distribute the reagents in the reaction volume. In the context of PCR, for example, the reagents are commonly mixed by pipetting the liquid up and down a number of times.

Mixing of components prior to or during PCR processes can present several challenges. For example, it can be difficult to incorporate a mixing mechanism in an enclosed sample-to-answer system. In addition, it may be desirable to mix components in certain processes in a precisely controlled manner to reduce the likelihood of emulsification of the reaction components.

Exemplary embodiments of the present disclosure provide for mixing of components in a precisely controlled manner. In addition, exemplary embodiments can be incorporated within the space limitations of PCR assemblies.

SUMMARY OF THE INVENTION

Exemplary embodiments of the present disclosure relate to systems and methods for mixing contents in a chamber via a magnetic coupling between components located within and outside of the chamber.

Particular embodiments relate to applying a magnetic field to move a magnetically responsive component in the chamber. The magnetically responsive component may be, for example, a ball, disk, or rod. In specific embodiments, magnetic mixing using the magnetically responsive component aids in one or more of: the displacement of air bubbles from the bottom or sides of the reaction volume, the resuspension of lyophilized reagents, and/or the inversion of wax that has not naturally inverted by disrupting the surface tension at the wax-resuspension buffer interface. In certain embodiments, the magnetically responsive component also disrupts the surface tension, which can allow for air bubbles to more easily escape from the liquid. Furthermore, magnetic mixing may be used continuously or intermittently in order to reduce temperature gradients in the reaction volume. This can be advantageous in, for example, applications like PCR that involve heating and/or cooling of the chamber. In particular embodiments, during the mixing process, a magnet moves towards the chamber, which lifts the magnetically responsive component to just under the meniscus of the liquid, and then the magnet moves away from the chamber either by a motion that directs the magnetically responsive component to the bottom of the chamber by magnetic attraction or by a motion whereby the magnetically responsive component falls to the bottom of the chamber due to gravity. In certain embodiments, the magnetically responsive component is held at its upper position (e.g., near the meniscus) for about 0, 1, 2, 3, 4, or 5 seconds, and is held at its lower position (e.g., at the bottom of the chamber) for about 0, 1, 2, 3, 4, or 5 seconds. In particular embodiments, the movement of the magnetically responsive component between its upper and lower positions can be continued for about 15, 30, 60, 90, 120, 180, 240 or 360 seconds, or between about 15 to 180 seconds, 30 to 120 seconds, or about 60 to 120 seconds, or about 60 to 240 seconds, or about 60 to 360 seconds in order to mix the contents of the chamber. In certain embodiments, the movement of the magnetically responsive component between its upper and lower positions is continuous or intermittent throughout the time of a reaction occurring in the chamber. In particular embodiments, the chamber has a volume of between 25 µl and 2 ml, 25 µl and 1 ml, 25 µl and 500 µl, 25 µl and 100 µl, 50 µl and 2 ml, 50 µl and 1 ml, or 50 µl and 500 µl.

Certain embodiments include an apparatus comprising: a shaft comprising a first end and a second end and a longitudinal axis extending between the first end and the second end; a motor coupled to the shaft, where the motor is configured to rotate the shaft about the longitudinal axis of the shaft; a magnet coupled to the shaft, where the magnet comprises a first end proximal to the longitudinal axis of the shaft and a second end distal to the longitudinal axis of the shaft; and a housing configured to receive a chamber. In particular embodiments, the shaft is configured to move from a first shaft position to a second shaft position, where, in the first shaft position, the second end of the magnet is distal from the housing, and in the second shaft position, the second end of the magnet is proximal to the housing.

In specific embodiments, the shaft is configured to rotate from the first shaft position to the second shaft position. In some embodiments, the housing comprises an insert configured to receive the chamber. Certain embodiments can further comprise a chamber received within the housing, and a moveable magnetically responsive component disposed within the chamber. In particular embodiments, the moveable magnetically responsive component is in a first position when the shaft is in the first shaft position, and the moveable magnetically responsive component is in a second position when the shaft is in the second shaft position.

In some embodiments, the moveable magnetically responsive component is in contact with the bottom surface of the chamber when the moveable magnetically responsive component is in the first position, and the moveable magnetically responsive component is in contact with the side surface (and not the bottom surface) of the chamber when the moveable magnetically responsive component is in the second position. In specific embodiments, the housing comprises a thermoelectric cooler (TEC). In certain embodiments, the chamber comprises a composition of stabilized lyophilized biological reagents. In particular embodiments, the side surface of the chamber is tapered and the bottom surface of the chamber is curved. In specific embodiments, the bottom surface is curved with a first radius; the moveable magnetically responsive component is a spherical ball with a second radius; and the first radius is greater than the second radius. In certain embodiments, the second radius (i.e., the radius of the ball) is at least 50%, 60%, 70%, 80%, or 90% (but less than 100%) of the first radius (i.e., the radius of the bottom surface).

In particular embodiments, the moveable magnetically responsive component is a ball, a disk, or a rod. In certain aspects, the magnetically responsive component may have a diameter or length in its longest dimension of between about 0.5 mm to about 5 mm, or between about 1 mm to about 2 mm. In some embodiments, the rod has a length between approximately 0.0625 inches and 0.125 inches. In specific embodiments, the moveable magnetically responsive component is a stainless steel ball. In particular embodiments, the stainless steel ball is a 400 series stainless steel ball. In some embodiments the ball has a diameter of about 1.6 mm. In some embodiments, the stainless steel object (e.g., ball, disk, or rod) has been passivated to remove free iron or other inclusions from its surface. Stainless steel can be passivated by, for example, a series of acid baths, which clean free iron or other inclusions from the surface, and form a uniform natural oxide layer that protects the stainless steel from corrosion. The magnetically responsive component is preferably made of, or at least coated with, a material that is inert to the reaction conditions in which it is present. In certain aspects, magnetic or magnetically responsive materials may be encased in or coated with non-magnetically responsive material in order to prevent their interaction with the reaction environment. For example, the magnetic or magnetically responsive materials may be encased in or coated with ceramic, glass, or plastic (e.g., polystyrene, polyethylene, polyethene, polypropylene, neoprene, poly(tetrafluoroethylene)).

In certain embodiments, the chamber comprises contents suitable for use in a polymerase chain reaction (PCR) nucleic acid amplification process and the moveable magnetically responsive component is passivated to form an oxide layer that is non-reactive with contents of the chamber. In particular embodiments, the chamber comprises reagents suitable for use in polymerase chain reaction (PCR) nucleic acid amplification process.

In some embodiments, the first shaft position is approximately, 15, 20, 25, 30, 35, 50, 60, 70, 80, or 90 degrees from the second shaft position. In some embodiments, the first shaft position is between about 15 to 90 degrees, 20 to 50 degrees, or 20 to 30 degrees from the second shaft position. Specific embodiments further comprise a switch configured to limit rotation of the shaft between the first shaft position and the second shaft position. In certain embodiments, the switch is an optical switch comprising a disc coupled to the shaft. In particular embodiments, the apparatus is coupled to a polymerase chain reaction (PCR) control module configured to control rotation of the shaft between the first shaft position and the second shaft position. In some embodiments, the PCR control module is configured to control rotation of the shaft from the first shaft position to the second shaft position such that the moveable magnetically responsive component is held in the first position for approximately 0, 1, 2, 3, 4, 5 seconds (or any range therein) and then moved to the second position and held in the second position for approximately 0, 1, 2, 3, 4, 5 seconds (or any range therein). In specific embodiments, the PCR control module is configured to control rotation of the shaft from the first shaft position to the second shaft position such that the moveable magnetically responsive component is cycled between the first and second positions for approximately 15, 30, 60, 90, 120, 180, 240 or 360 seconds (or any range therein). In some embodiments, the PCR control module is configured to control rotation of the shaft from the first shaft position to the second shaft position such that the moveable magnetically responsive component is cycled between the first and second positions prior to concurrent with the start of the PCR (e.g., during an initial denaturation step or during a reverse transcription phase if it is an RT-PCR), intermittently during the PCR (e.g., mixing during temperature changes to reduce thermal gradients in the reaction), or continuously during all or a substantial portion of the PCR.

In certain embodiments, the magnet has a maximum energy product (BHmax) of between 48 and 54 Megagauss-Oersteds (MGOe). In some embodiments, the magnet has a maximum energy product (BHmax) of approximately 52 MGOe. In particular embodiments, the second end of the magnet is located approximately 0.70, 0.75, 0.80, 0.82, 0.85, or 0.90 (or any range therein) inches from the longitudinal axis of the rotating shaft. In some embodiments, the second end of the magnet is approximately 0.10, 0.15, 0.20, 0.21, 0.22, or 0.25 (or any range therein) inches from a centroid of the moveable magnetically responsive component when the system is in the first shaft position. The apparatus may be configured such that the magnet is only close enough to magnetically attract the magnetically responsive component when the magnet is in the second position or it may be configured such that the magnet is close enough to magnetically attract the magnetically responsive component when the magnet is in both the second and first positions. Magnetically attracting the magnetically responsive component to its lower position provides the ability, if desired, to move the magnetically responsive component to the lower position faster than with gravity alone. In specific embodiments, the magnet is longitudinally magnetized. In certain embodiments, the magnet is a made of neodymium. In particular embodiments, the magnet is cylindrical in shape, with a diameter of approximately 0.125 inches and a length of 0.375 inches. In some embodiments, the housing comprises a first opening configured to receive the magnet such that the second end of the magnet extends into the first opening when the shaft is in the second shaft position. In certain embodiments, the second end of the magnet also may extend into or partially into the first opening when the shaft is in the first shaft position. In specific embodiments, the housing comprises a second opening configured to receive a chamber. In particular embodiments, the housing comprises a third opening configured to receive a fiber-optic cable. In some embodiments, the housing comprises a fourth opening configured to receive a second fiber-optic cable. In certain embodiments, the housing comprises an insert defining a conical space.

Some embodiments include an apparatus comprising: a shaft comprising a first end and a second end and a longitudinal axis extending between the first end and the second end; a motor coupled to the shaft, wherein the motor is configured to rotate the shaft about the longitudinal axis of the shaft; a plurality of magnets coupled to the shaft along the longitudinal axis of the shaft, wherein each magnet comprises a first end proximal to the longitudinal axis of the shaft and a second end distal to the longitudinal axis of the shaft; and a module comprising a plurality of housings arranged along a linear axis. The module may comprise, for example, 4 to 24 housings, 4 to 12 housings, 4 to 8 housings, 4 to 6 housings, 6 to 24 housings, or 6 to 12 housings. In specific embodiments, the longitudinal axis of the shaft is substantially parallel to the linear axis of the plurality of housings; and each magnet of the plurality of magnets is aligned with a corresponding housing of the plurality of housings.

In certain embodiments, the shaft is configured to rotate from a first shaft position in which the second end of each magnet is distal from the corresponding housing; and the shaft is configured to rotate to a second shaft position in which the second end of each magnet is proximal from the corresponding housing. Particular embodiments further comprise: a chamber disposed within each housing of the plurality of housings; and a moveable magnetically responsive component disposed within each chamber. In some embodiments, the second end of each magnet is distal to a side surface of the chamber when the shaft is in the first position; and the second end of each magnet is proximal to a side surface of the chamber and distal to the bottom surface of the chamber when the shaft is in the second position. In specific embodiments, the moveable magnetically responsive component in each chamber is in a first position in contact with a bottom surface of the chamber when the shaft is in the first shaft position; and the moveable magnetically responsive component in each chamber is in a second position in contact with a side surface of the chamber and not in contact with a bottom surface of the chamber when the shaft is in the second shaft position.

In certain embodiments, the side surface of each chamber is tapered and the bottom surface of each chamber is curved. In particular embodiments, the housing comprises a thermoelectric cooler (TEC). In some embodiments, each chamber comprises a composition of stabilized lyophilized biological reagents comprising a lyophilized pellet comprising nucleoside triphosphates (NTPs) and a polymerase enzyme. In particular embodiments, the moveable magnetically responsive component is a stainless steel ball. In certain aspects, the magnetically responsive component may have a diameter or length in its longest dimension of between about 0.5 mm to about 5 mm, or between about 1 mm to about 2 mm. In some embodiments, the moveable magnetically responsive component is a sphere (i.e., ball) with a diameter of approximately 0.0625 inches. In specific embodiments, each chamber comprises contents suitable for use in a polymerase chain reaction (PCR) nucleic acid amplification process and wherein the moveable magnetically responsive component is passivated to form an oxide layer that is non-reactive with contents of the chamber. In certain embodiments, each chamber comprises reagents suitable for use in polymerase chain reaction (PCR) nucleic acid amplification process. In particular embodiments, each chamber further comprises a liquid.

In some embodiments, the moveable magnetically responsive component in each chamber is in a first position in contact with a bottom surface of the chamber when the shaft is in the first shaft position; the moveable magnetically responsive component in each chamber is in a second position that contacts a side surface of the chamber when the shaft is in the second shaft position; and the second position of the moveable magnetically responsive component is located between the surface of the liquid and the bottom surface of the chamber. In specific embodiments, the first shaft position is approximately 15, 20, 25, 30, 35, 50, 60, 70, 80, or 90 degrees from the second shaft position. In some embodiments, the first shaft position is between about 15 to 90 degrees, 20 to 50 degrees, or 20 to 30 degrees from the second shaft position.

Certain embodiments further comprise a switch configured to limit rotation of the shaft between the first shaft position and the second shaft position. In particular embodiments, the switch is an optical switch comprising a disc coupled to the shaft. In some embodiments, the apparatus is coupled to a polymerase chain reaction (PCR) control module configured to control rotation of the shaft between the first shaft position and the second shaft position. In specific embodiments, the PCR control module is configured to control rotation of the shaft from the first shaft position to the second shaft position such that the moveable magnetically responsive component is held in the first position for approximately 0, 1, 2, 3, 4, 5 seconds (or any range therein) and then moved to the second position and held in the second position for approximately 0, 1, 2, 3, 4, 5 seconds (or any range therein). In certain embodiments, the PCR control module is configured to control rotation of the shaft from the first shaft position to the second shaft position such that the moveable magnetically responsive component is cycled between the first and second positions for approximately 15, 30, 60, 90, 120, 180, 240 or 360 seconds (or any range therein). In some embodiments, the PCR control module is configured to control rotation of the shaft from the first shaft position to the second shaft position such that the moveable magnetically responsive component is cycled between the first and second positions prior to concurrent with the start of the PCR (e.g., during an initial denaturation step or during a reverse transcription phase if it is an RT-PCR), intermittently during the PCR (e.g., mixing during temperature changes to reduce thermal gradients in the reaction), or continuously during all or a substantial portion of the PCR.

Other embodiments include methods of mixing reagents using an apparatus as disclosed herein. The method may comprise, for example: obtaining an apparatus comprising: a chamber containing a magnetically responsive component and reagents; and a magnet coupled to a rotating shaft, where: the shaft is configured to move from a first shaft position to a second shaft position; in the first shaft position, the second end of the magnet is distal from the chamber; and in the second shaft position, the second end of the magnet is proximal to the chamber; and moving the shaft from a first position to a second position, wherein the magnetically responsive component is moved within the chamber from a first position to a second position, thereby mixing the reagents. The reagents may be, for example, PCR reagents and/or reverse transcription reagents. In some embodiments, the reagents may comprise an enzyme. In certain embodiments, the enzyme may be a polymerase, an endonuclease, or an exonuclease. Certain embodiments include a method of mixing reagents during a polymerase chain reaction (PCR). In specific embodiments the method includes obtaining an apparatus comprising: a chamber containing a magnetically responsive component and reagents, wherein the reagents are suitable for PCR; and a magnet configured to move the magnetically responsive component between a first position in the chamber and a second position in the chamber (e.g. between a bottom surface of the chamber and a side surface of the chamber. Particular embodiments can include a magnet coupled to a rotating shaft, where the shaft is configured to move from a first shaft position to a second shaft position, and in the first shaft position, the second end of the magnet is distal from the chamber, and in the second shaft position, the second end of the magnet is proximal to the chamber. In certain embodiments, the method includes moving the shaft from a first position to a second position, wherein the magnetically responsive component is moved within the chamber from a first position to a second position, thereby mixing the reagents.

In particular embodiments, the chamber comprises a bottom surface and a side surface, and wherein the magnetically responsive component contacts the bottom surface in the first position and wherein the magnetically responsive component contacts the side surface in the second position. In some embodiments, the magnetically responsive component is moved from the first position to the second position and held in the second position for approximately 0, 1, 2, 3, 4, 5 seconds (or any range therein); and the magnetically responsive component is moved from the second position to the first position and held in the first position for approximately 0, 1, 2, 3, 4, 5 seconds (or any range therein). In specific embodiments, the magnetically responsive component is cycled between the first and second positions for approximately 15, 30, 60, 90, 120, 180, 240 or 360 seconds (or any range therein). In certain embodiments, the moveable magnetically responsive component is cycled between the first and second positions prior to or concurrent with the start of the PCR (e.g., during an initial denaturation step or during a reverse transcription phase if it is an RT-PCR), intermittently during the PCR (e.g., mixing during temperature changes to reduce thermal gradients in the reaction), or continuously during all or a substantial portion of the PCR. In particular embodiments, at least one of the reagents is provided in a lyophilized form. In some embodiments, the side surface of the chamber is tapered and the bottom surface of the chamber is curved. In specific embodiments of the method, the bottom surface is curved with a first radius; the moveable magnetically responsive component is a spherical ball with a second radius; and the first radius is greater than the second radius. Certain embodiments of the method comprise moving the magnetically responsive component prior to beginning a first PCR cycle. Particular embodiments comprise moving the magnetically responsive component during at least a portion of each PCR cycle.

In some embodiments, the movement of the magnetically responsive component occurs during a temperature ramping phase. In specific embodiments, movement of the magnetically responsive component from the first position to the second position reduces a temperature gradient in the chamber. Certain embodiments comprise moving the magnetically responsive component prior to and during a polymerase chain reaction. Particular embodiments comprise moving the magnetically responsive component prior to beginning a reverse transcription reaction. Some embodiments comprise moving the magnetically responsive component during at least a portion of a reverse transcription reaction. Specific embodiments comprise moving the magnetically responsive component prior to and during a polymerase chain reaction.

In certain embodiments, movement of the magnetically responsive component from the first position to the second position inverts a melted wax layer in the chamber. In particular embodiments of the methods, the magnetically responsive component is a sphere. In some embodiments of the method, the sphere has a diameter of approximately 0.0625 inches. In specific embodiments of the method, the magnetically responsive component is a disk or a sphere having a first diameter, and wherein a distance from first position to the second position of the magnetically responsive component is between two and five times the first diameter. In certain embodiments, the reagents are polymerase chain reaction (PCR) reagent. In particular embodiments, the reagents are reverse transcription reagents. In some embodiments, the reagents comprise an enzyme, and in specific embodiments, the enzyme is a polymerase, endonuclease, or a exonuclease.

Certain embodiments include an apparatus comprising: a housing; an insert disposed within the housing, wherein the insert is configured to receive a chamber; a first electromagnet proximal to a first location on the insert; and a second electromagnet proximal to a second location on the insert. In particular embodiments, the first and second electromagnets are configured to alternatingly and respectively apply a magnetic force to the first and second locations on the insert. In some embodiments, the insert comprises a conical space defined by a tapered side surface having a first end and a second end; the first end is larger in diameter than the second end; the first end is open and the second end is closed; the first location on the insert is located between the first end and the second end of the insert; and the second location is located proximal to the second end of the insert.

Some embodiments further comprise: a chamber received within the insert; and a moveable magnetically responsive component disposed within the chamber. In specific embodiments, the moveable magnetically responsive component is in a first position when the first electromagnet is activated to apply a magnetic force; and the moveable magnetically responsive component is in a second position when the second electromagnet is activated to apply a magnetic force. In certain embodiments, the chamber comprises contents suitable for use in a polymerase chain reaction (PCR) nucleic acid amplification process and the moveable magnetically responsive component is passivated to form an oxide layer that is non-reactive with contents of the chamber. In particular embodiments, the chamber comprises reagents suitable for use in polymerase chain reaction (PCR) nucleic acid amplification process.

Certain embodiments include an apparatus comprising: a housing; an insert disposed within the housing, wherein the insert is configured to receive a chamber; and an electromagnet proximal to a first location on the insert, where the electromagnet is configured to alternatingly apply a magnetic force to the location on the insert. In specific embodiments, the insert comprises a conical space defined by a tapered side surface having a first end and a second end; the first end is larger in diameter than the second end; the first end is open and the second end is closed; and the first location on the insert is located between the first end and the second end of the insert.

Certain embodiments further comprise: a chamber received within the insert; and a moveable magnetically responsive component disposed within the chamber. In particular embodiments, the moveable magnetically responsive component is in a first position when the electromagnet is energized to apply a magnetic force; and the moveable magnetically responsive component is in a second position when the electromagnet is not energized to apply a magnetic force. In certain embodiments, the chamber comprises contents suitable for use in a polymerase chain reaction (PCR) nucleic acid amplification process and the moveable magnetically responsive component is passivated to form an oxide layer that is non-reactive with contents of the chamber. In particular embodiments, the chamber comprises reagents suitable for use in polymerase chain reaction (PCR) nucleic acid amplification process.

The term "coupled" is defined as connected, although not necessarily directly, and not necessarily mechanically. Two items are "coupleable" if they can be coupled to each other, and, when coupled, may still be characterized as "coupleable." Unless the context explicitly requires otherwise, items that are coupleable are also decoupleable, and vice-versa. One non-limiting way in which a first structure is coupleable to a second structure is for the first structure to be configured to be coupled (or configured to be coupleable) to the second structure.

The terms "a" and "an" are defined as one or more unless this disclosure explicitly requires otherwise.

The term "substantially" and its variations (e.g., "approximately" and "about") are defined as being largely but not necessarily wholly what is specified (and include wholly what is specified) as understood by one of ordinary skill in the art. In any disclosed embodiment, the terms "substantially," "approximately," and "about" may be substituted with "within [a percentage] of" what is specified, where the percentage includes 0.1, 1, 5, and 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements possesses those one or more steps or elements, but is not limited to possessing only those one or more elements. Likewise, a step of a method or an element of a device that "comprises," "has," "includes" or "contains" one or more features possesses those one or more features, but is not limited to possessing only those one or more features. For example, a system that comprises an ultrasonic transducer has one sample reservoir unit, but may have more than one ultrasonic transducer.

Furthermore, a device or structure that is configured in a certain way is configured in at least that way, but may also be configured in ways that are not listed. Metric units may be derived from the English units provided by applying a conversion and rounding to the nearest millimeter.

The feature or features of one embodiment may be applied to other embodiments, even though not described or illustrated, unless expressly prohibited by this disclosure or the nature of the embodiments.

Any embodiment of any of the disclosed devices and methods can consist of or consist essentially of—rather than comprise/include/contain/have—any of the described elements and/or features and/or steps. Thus, in any of the claims, the term "consisting of" or "consisting essentially of" can be substituted for any of the open-ended linking verbs recited above, in order to change the scope of a given claim from what it would otherwise be using the open-ended linking verb.

Other features and associated advantages will become apparent with reference to the following detailed description of specific embodiments in connection with the accompanying drawings.

BRIEF DESCRIPTION OF THE DRAWINGS

The following drawings illustrate by way of example and not limitation. For the sake of brevity and clarity, every feature of a given structure may not be labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Figure 1:
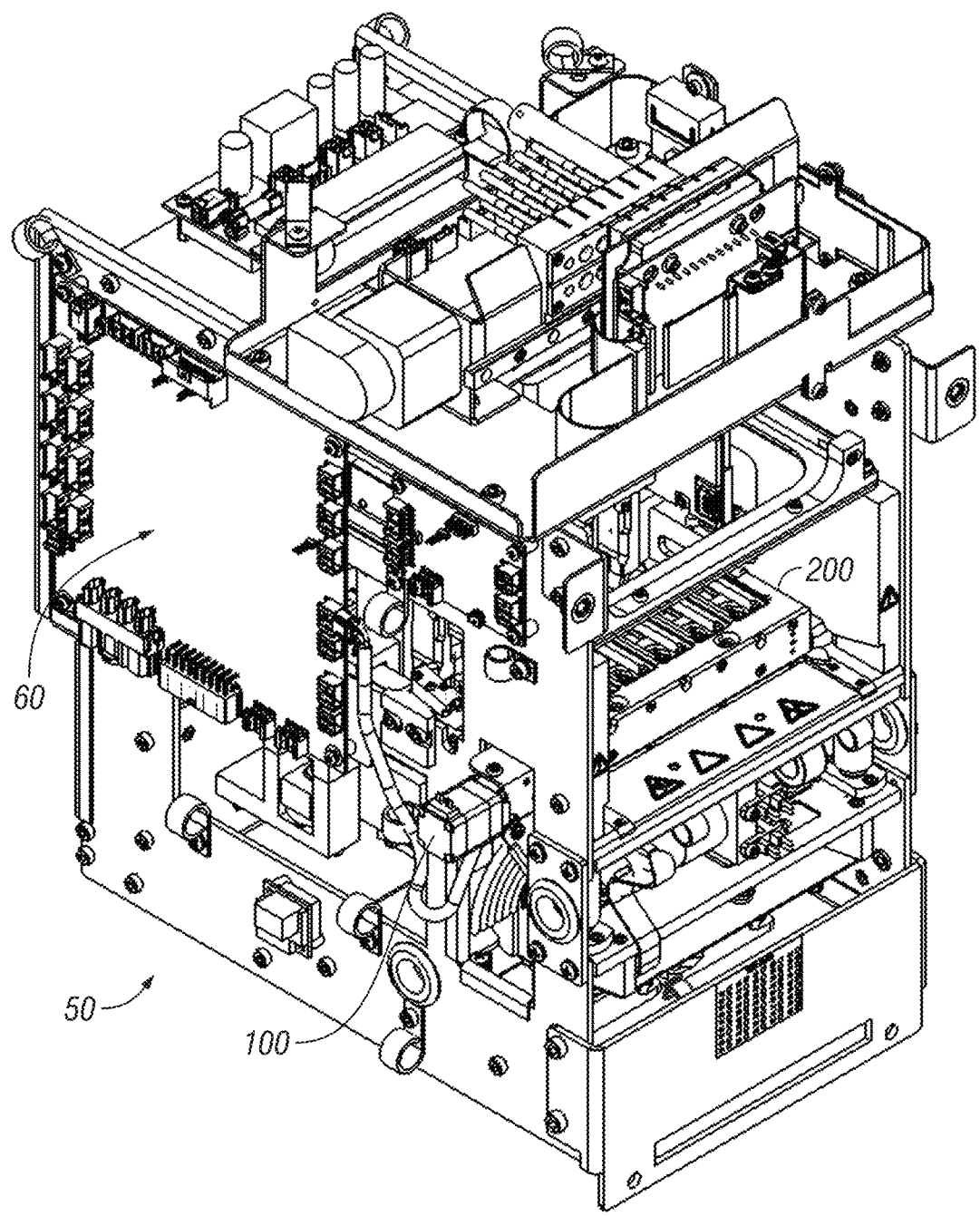
FIG. 1 is perspective view of a polymerase chain reaction (PCR) modular assembly comprising a magnetic actuation assembly and thermo-electric cooler (TEC) sub-assembly according to exemplary embodiments of the present disclosure.
Figure 2:
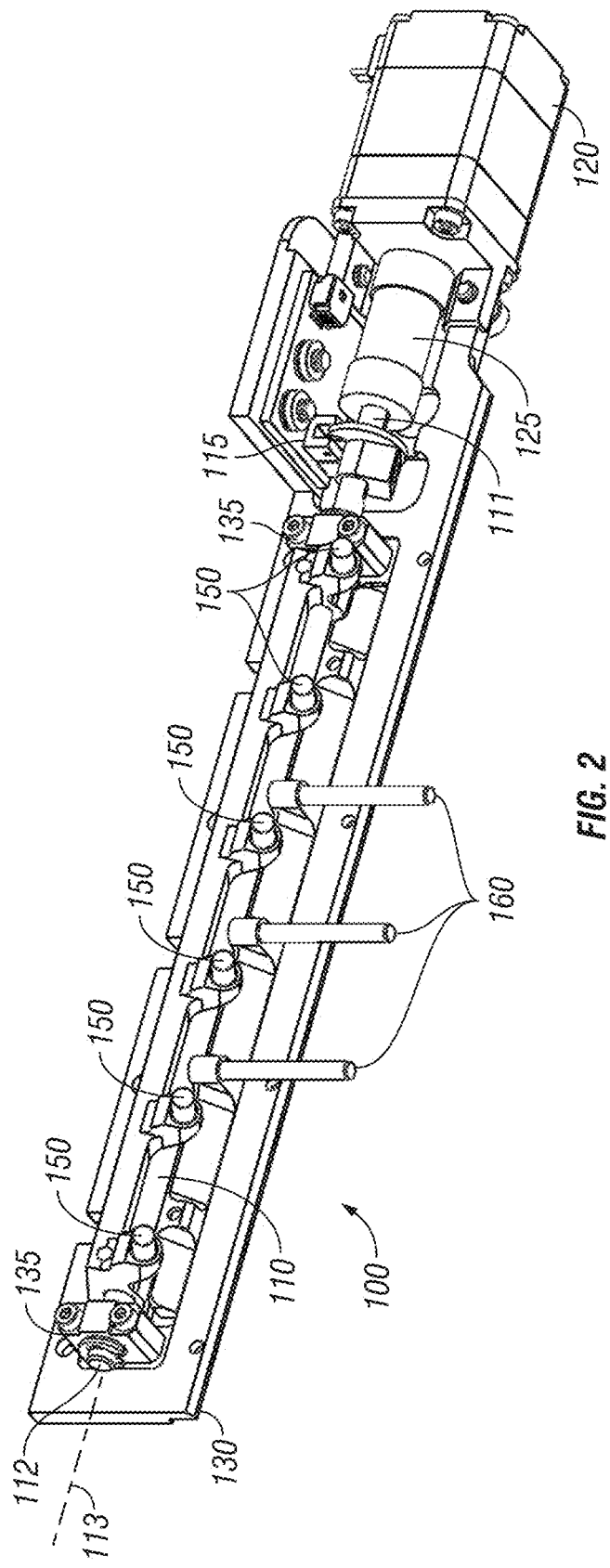
FIG. 2 is a perspective view of the magnetic actuation assembly of the embodiment of FIG. 1.

Various features and advantageous details are explained more fully with reference to the non-limiting embodiments that are illustrated in the accompanying drawings and detailed in the following description. It should be understood, however, that the detailed description and the specific examples, while indicating embodiments of the invention, are given by way of illustration only, and not by way of limitation. Various substitutions, modifications, additions, and/or rearrangements will become apparent to those of ordinary skill in the art from this disclosure.

In the following description, numerous specific details are provided to provide a thorough understanding of the disclosed embodiments. One of ordinary skill in the relevant art will recognize, however, that the invention may be practiced without one or more of the specific details, or with other methods, components, materials, and so forth. In other instances, well-known structures, materials, or operations are not shown or described in detail to avoid obscuring aspects of the invention. It is understood that for purposes of clarity, not all reference numbers are shown for every component visible in each figure.

Referring initially to FIGS. 1-6, a polymerase chain reaction (PCR) modular assembly 50 configured for nucleic acid amplification comprises a magnetic actuation assembly 100 coupled to a thermo-electric cooler (TEC) sub-assembly 200. In the embodiment shown, (PCR) modular assembly 50 also comprises a PCR control module 60 configured to control magnetic actuation assembly 100, including for example, the movement or rotation of a shaft 110 of magnetic actuation assembly 100.

Referring particularly now to FIGS. 2-6, magnetic actuation assembly 100 comprises shaft 110 coupled to an electric motor 120 via a coupling 125 (e.g., a bellows coupling). In the embodiment shown, magnetic actuation assembly 100 also comprises a support plate 130 and support members 135 that support shaft 110. In particular embodiments, support members 135 can be configured as pillow blocks containing plastic bushings. Magnetic actuation assembly 100 may also comprise one or more switches 115 that can limit rotation of shaft 110, as explained in further detail below.

In the embodiment shown, shaft 110 comprises a first end 111 and a second end 112 with a longitudinal axis 113 extending between the first and second end. The embodiment shown also comprises a plurality of magnets 150 coupled to shaft 110 along longitudinal axis 113.

Figure 4:
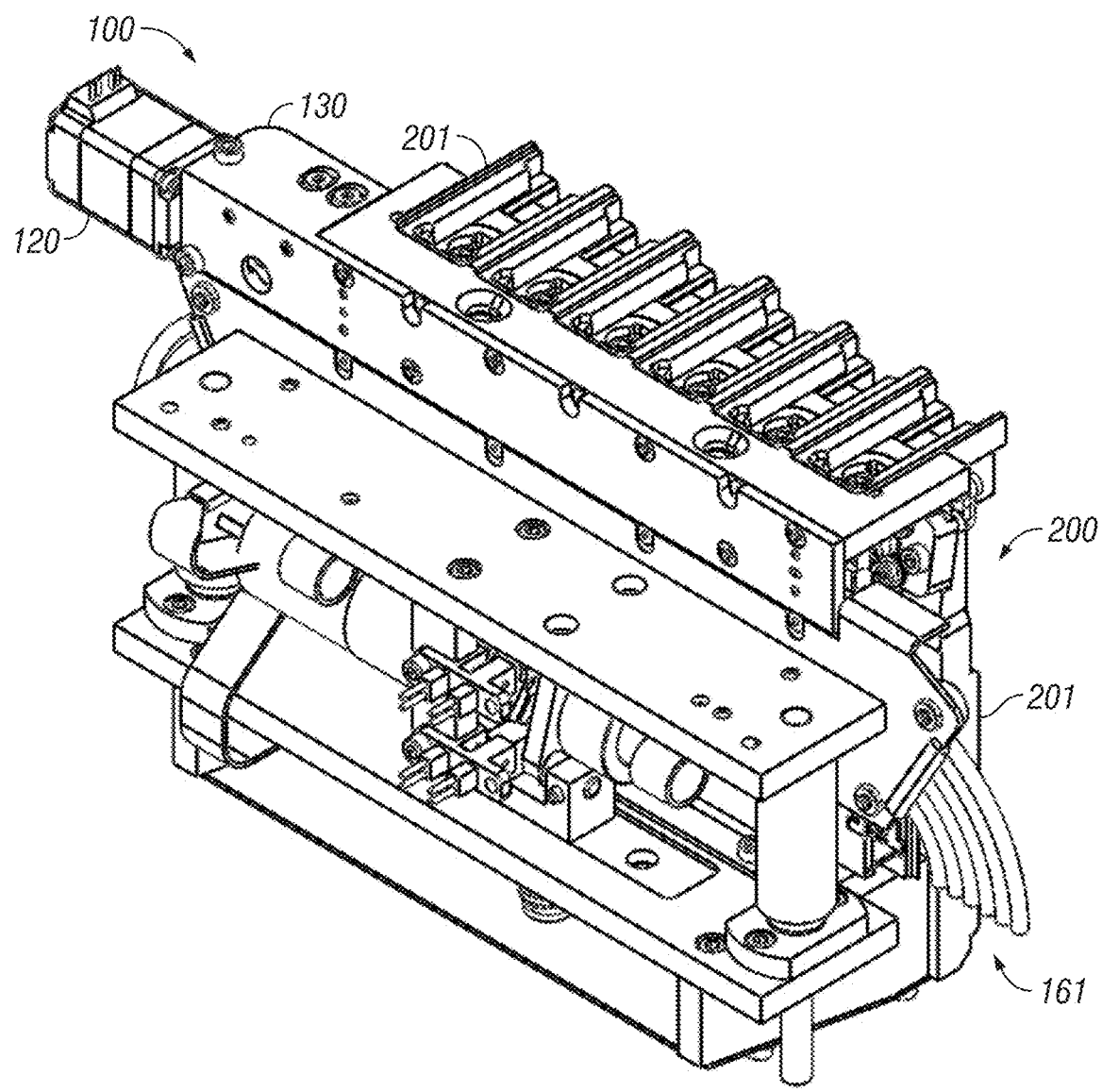
FIG. 4 is a first perspective view of the magnetic actuation assembly and the (TEC) sub-assembly of the embodiment of FIG. 1.
Figure 5:
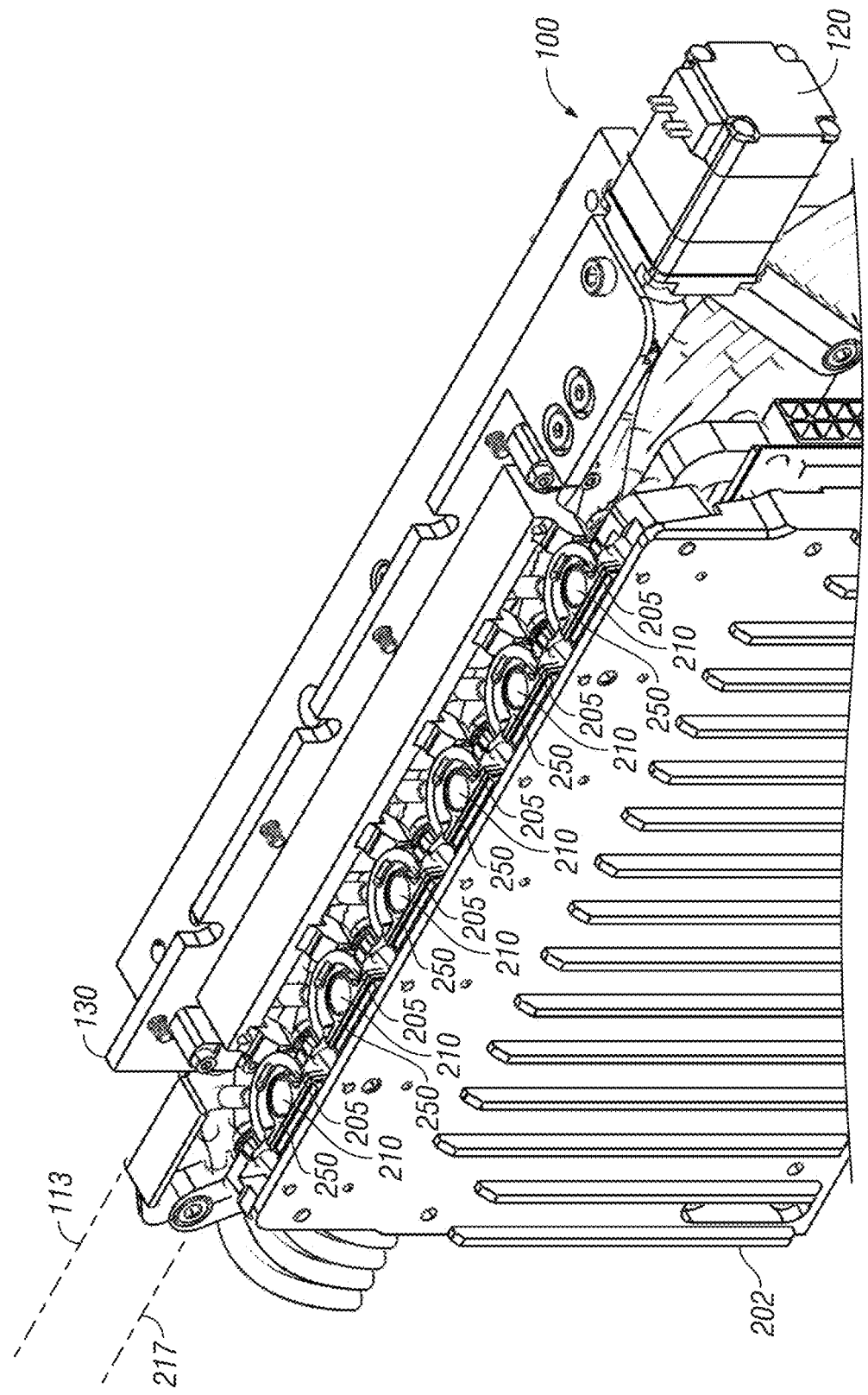
FIG. 5 is a second perspective view of a partial magnetic actuation assembly and the (TEC) sub-assembly of the embodiment of FIG. 1.

Magnetic actuation assembly 100 also comprises a plurality of retention members 160 configured to retain other components (e.g. fiber-optic cables 161) from interfering with operation of magnetic actuation assembly 100. As shown in FIGS. 4 and 5, TEC sub-assembly 200 can also comprise a heating module 201 and a heat sink 202.

Figure 3:
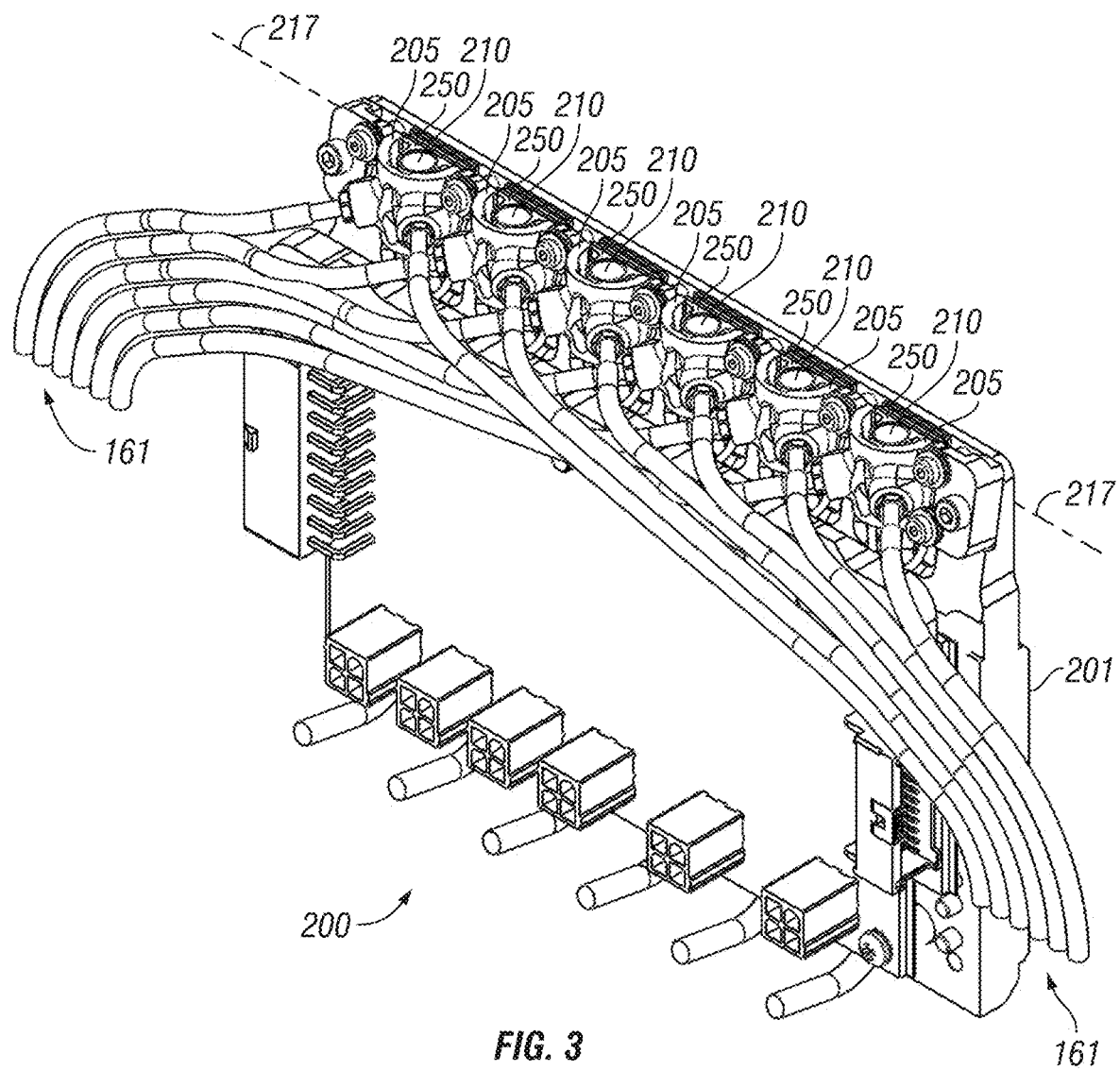
FIG. 3 is a perspective view of the (TEC) sub-assembly of the embodiment of FIG. 1.
Figure 6:
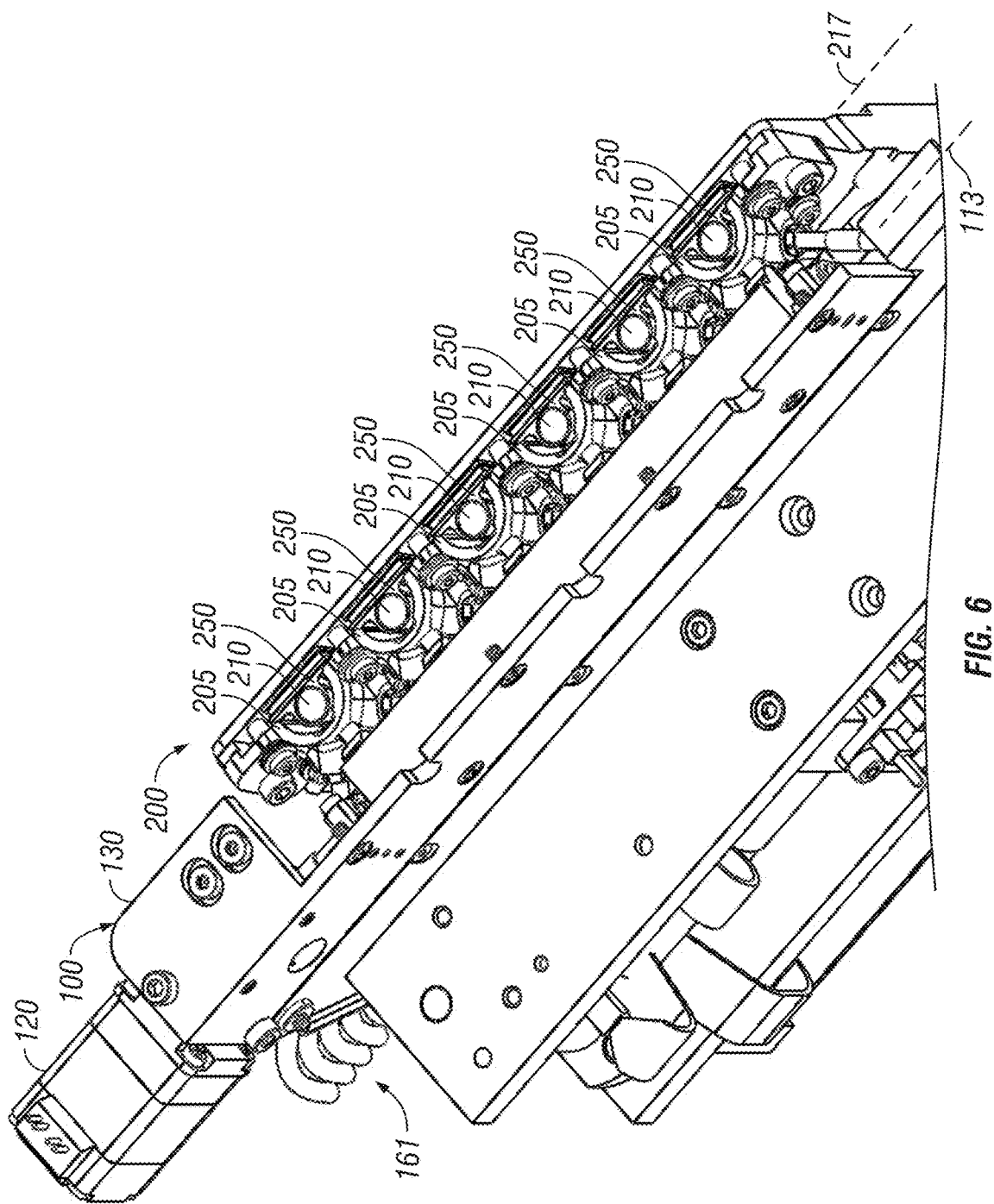
FIG. 6 is a third perspective view of a partial magnetic actuation assembly and the (TEC) sub-assembly of the embodiment of FIG. 1.
Figure 7:
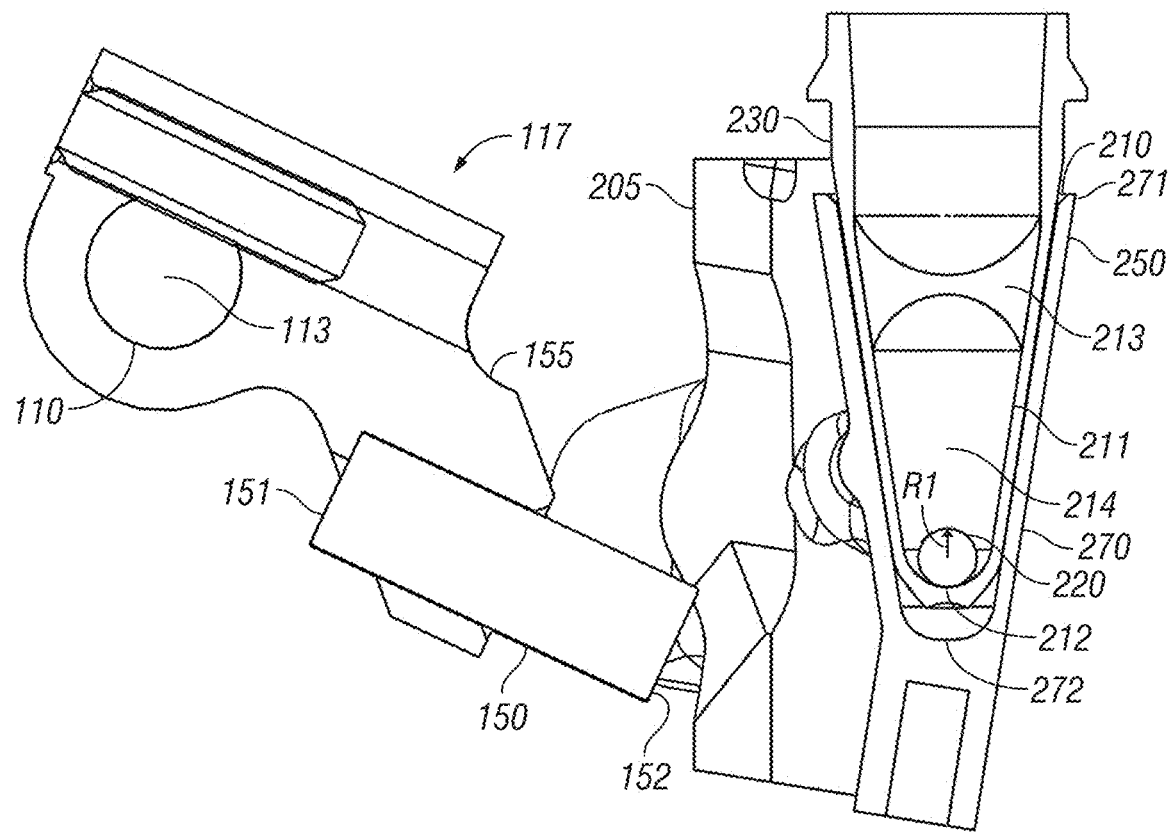
FIG. 7 is a partial section view of the magnetic actuation assembly and the (TEC) sub-assembly of the embodiment of FIG. 1 in a first position.
Figure 8:
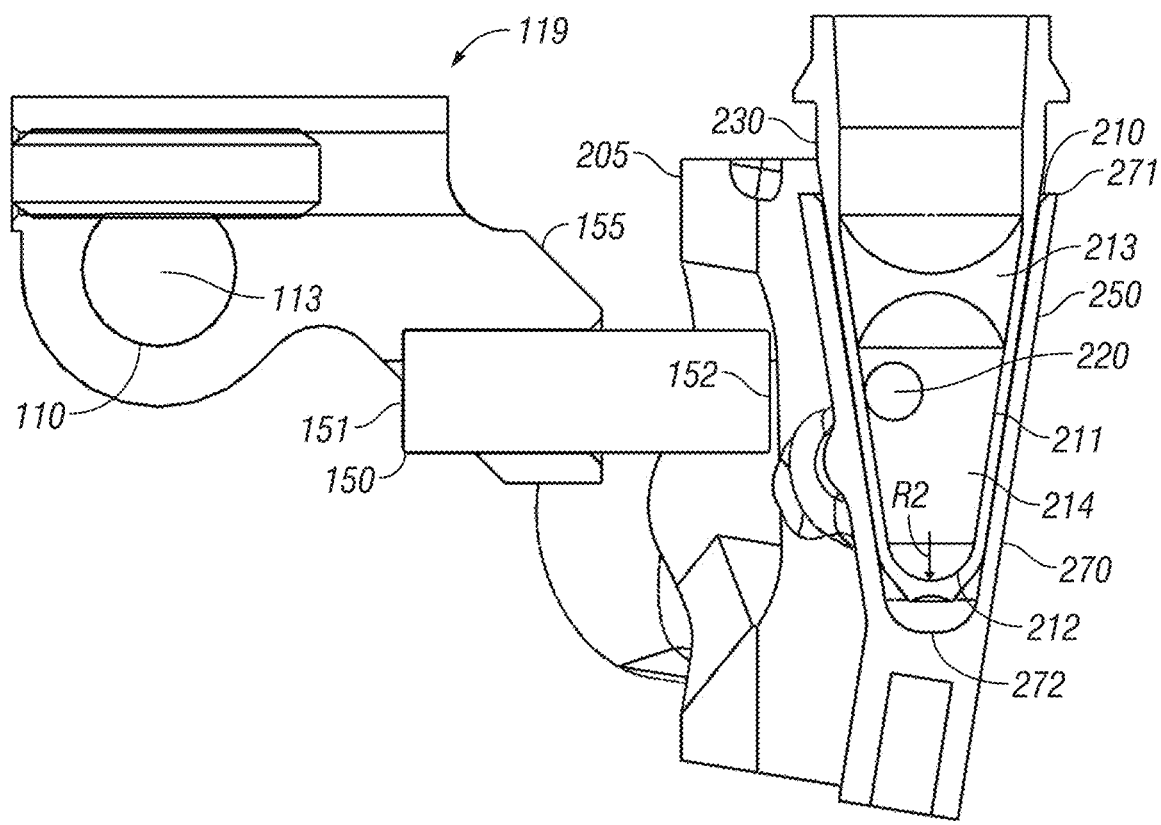
FIG. 8 is a partial section view of the magnetic actuation assembly and the (TEC) sub-assembly of the embodiment of FIG. 1 in a second position.

As shown in FIGS. 3 and 6, TEC sub-assembly 200 comprises a plurality of inserts 250 each disposed within a housing 205. In exemplary embodiments, inserts 250 can be configured as aluminum TEC blocks configured to conduct thermal energy to a chamber 230 (e.g. a PCR tube) as shown in FIGS. 7 and 8. Housing 205 may be configured as a TEC block insulator in exemplary embodiments.

As shown in FIGS. 7 and 8, an insert 250 can be configured to receive a chamber 230. In particular embodiments, insert 250 comprises a conical space 210 configured to receive chamber 230. In the embodiment shown, conical space 210 of insert 250 is defined by a tapered side surface 270 having a first end 271 that is larger and open, and a second end 272 that is smaller and closed. In the embodiment shown, the plurality of housings 205 are arranged along a linear axis 217 that is substantially parallel to longitudinal axis 113 of shaft 110 (shown in FIG. 5). In the illustrated embodiment each magnet 150 is aligned with a corresponding housing 205.

In particular embodiments, each chamber 230 comprises a side surface 211 that is tapered and a bottom surface 212 that is curved, such that side surface 211 and bottom surface 212 form a generally conical structure. It is understood that the terms "side surface" and "bottom surface" used throughout this disclosure are used only for reference purposes with respect to the drawings. For example, bottom surface 212 does not necessarily have to be at an absolute lowest portion of chamber 230, depending on the orientation of chamber 230. During operation, chambers 230 may comprise many different components used for PCR nucleic acid amplification. For example chambers 230 may comprise reagents including buffers, nucleotides, modified nucleotides, primers, probes, enzymes, sugars, and stabilizers.

In certain instances, it can be desirable to ensure the reagents are sufficiently mixed together to promote efficiency and accuracy in the PCR process. However, mixing of the components can also create undesirable effects. For example, mixing can create bubbles that interfere with the optical detection by fiber-optic cables 161. In addition, certain PCR processes can include an insulating layer 213 (e.g. an oil or wax layer) on top of the reagents 214 to reduce evaporation. In specific embodiments, insulating layer 213 may comprise 25 of docosane wax or mineral oil. If the mixing process is not properly controlled, insulating layer 213 can become emulsified with reagents 214, thereby increasing evaporation and reducing accuracy in the PCR detection and analysis.

Embodiments of the present disclosure provide for mixing of the PCR reagents in a controlled manner that reduces the likelihood of unwanted bubble formation or emulsification of insulating layer 213 and reagents 214. Particular embodiments comprise a moveable magnetically responsive component 220 disposed within a chamber 230. In certain embodiments, moveable magnetically responsive component 220 may be configured as a magnetic 400 series stainless steel (e.g. 440C grade) ball that is passivated to form a non-reactive oxide layer. In specific embodiments, moveable magnetically responsive component 220 may be sized in relation to the dimensions of bottom surface 212 of chamber 230. For example, moveable magnetically responsive component 220 can be a magnetic ball sized to engage the lowest portion of bottom surface 212 (e.g. the portion distal from insulating layer 213) without simultaneously engaging tapered side surface 211. In particular, moveable magnetically responsive component 220 can be a spherical or ball shape with a radius R1 that is less than a radius R2 of bottom surface 212. This can allow moveable magnetically responsive component 220 to adequately engage and mix the contents throughout chamber 230 without trapping bubbles between moveable magnetically responsive component 220 and bottom surface 212. In specific embodiments, moveable magnetically responsive component 220 can be configured as a spherical ball having a 1/16 (0.0625) inch diameter (i.e. a 1/32 or 0.03125 inch radius).

Referring now to FIGS. 7-10, magnetic actuation assembly 100 can be actuated such that shaft 110 is moved (e.g. rotated) from a first shaft position 117 to a second shaft position 119. As shown in FIGS. 7 and 8, magnet 150 is coupled to shaft 110 via a coupler 155 that spaces magnet 150 away from axis 113 of shaft 110. In this embodiment, each magnet 150 comprises a first end 151 proximal to longitudinal axis 113 and a second end 152 distal to longitudinal axis 113. Such a configuration allows second end 152 to swing in a wider rotational arc than first end 151 as shaft 110 is rotated.

In the embodiment shown, switch 115 (shown in FIG. 2) can limit rotation of shaft 110 between first shaft position 117 and second shaft position 119. In particular embodiments, switch 115 may be configured as an optical switch that limits rotation of shaft 110 to approximately 25 degrees between the first shaft position and the second shaft position. In specific embodiments, switch 115 may comprise a disc 116 that breaks an optical path within switch 115 to control rotation of shaft 110.

In first shaft position 117 (shown in FIGS. 7 and 9) second end 152 of magnet 150 is distal from chamber 230. In the first position, moveable magnetically responsive component 220 also contacts bottom surface 212 of chamber 230. In particular embodiments, magnet 150 may be an axially-magnetized magnet. Such a configuration can allow magnet 150 to exert a magnetic force on moveable magnetically responsive component 220 towards bottom surface 212 when shaft 110 is in the first position. This can help overcome viscosity drag forces between moveable magnetically responsive component 220 and reagents 214 and assist moveable magnetically responsive component 220 to contact bottom surface 212. In certain cases, the force of gravity alone may not be sufficient to overcome the viscous forces to ensure contact between moveable magnetically responsive component 220 and bottom surface 212.

In second shaft position 119 of shaft 110 (shown in FIGS. 8 and 10), second end 152 of magnet 150 is proximal to chamber 230 and moveable magnetically responsive component 220 contacts side surface 211 of chamber 230 as a result of the magnetic force exerted by magnet 150. As shown in FIG. 8, in second shaft position 119, moveable magnetically responsive component 220 is located below an interface 215 of insulating layer 213 and reagents 214 (e.g. between interface 215 and bottom surface 212). The relocation of moveable magnetically responsive component 220 between the first position contacting bottom surface 212 and the second position contacting side surface 211 can promote mixing of the contents of chamber 230.

Figure 9:
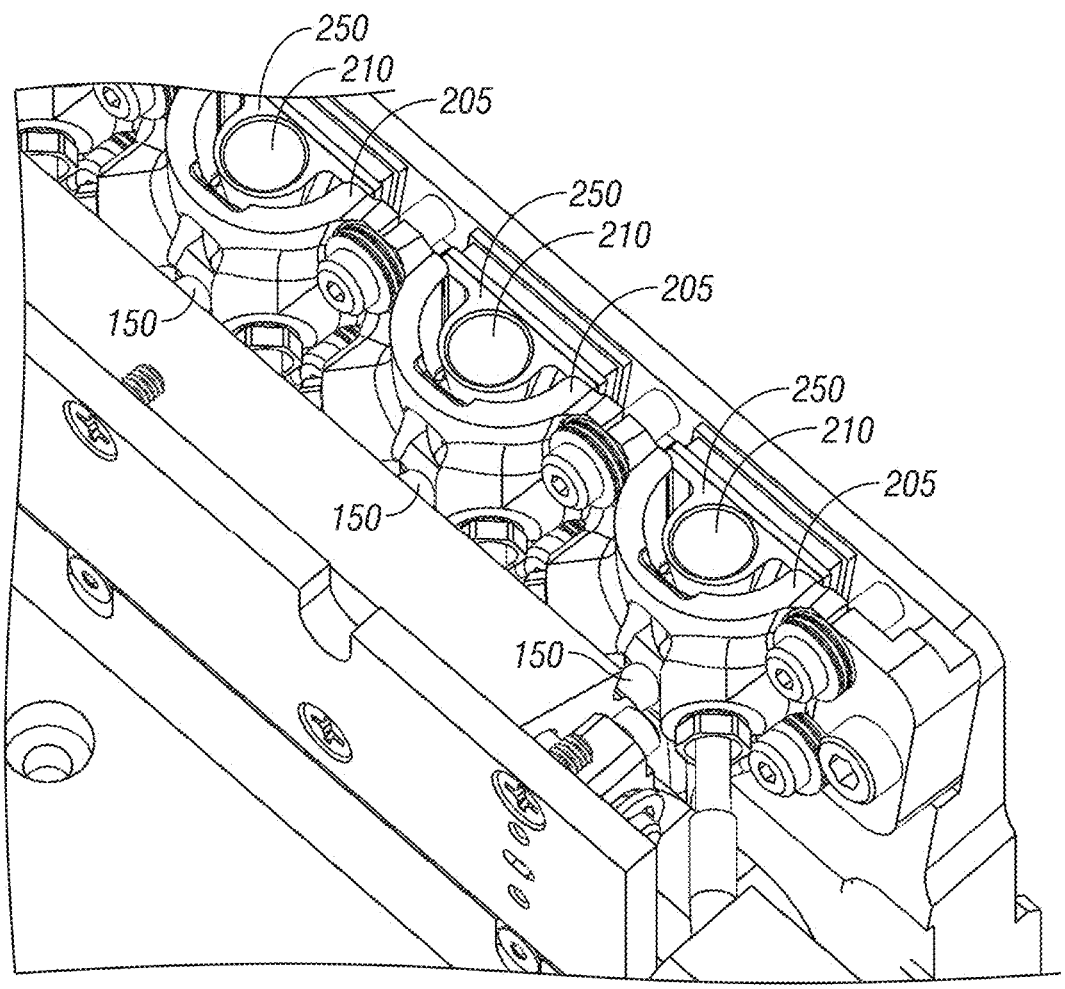
FIG. 9 is a partial perspective view of the magnetic actuation assembly and the (TEC) sub-assembly of the embodiment of FIG. 1 in a first position.
Figure 10:
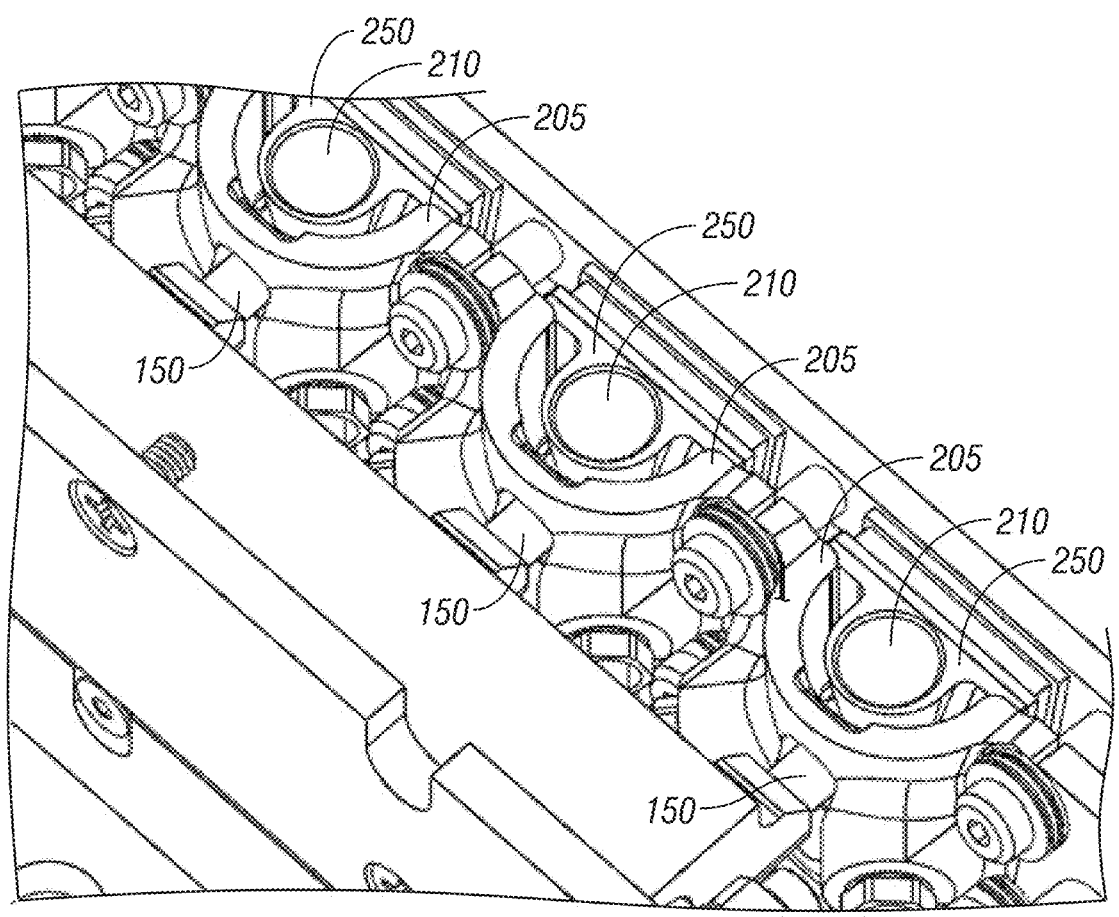
FIG. 10 is a partial perspective view of the magnetic actuation assembly and the (TEC) sub-assembly of the embodiment of FIG. 1 in a second position.

As shown in FIGS. 3, 9 and 10, each housing 205 may include a slot or opening 206 facing a magnet 150. In the first position shown in FIG. 9, magnet 150 is proximal to the lower portion of opening 206, and in the second position shown in FIG. 10, magnet 150 extends into opening 206 and is proximal to the upper end of opening 206. Opening 206 is configured to receive magnet 150 such that second end 152 of magnet 150 extends into opening 206 when shaft 110 is in second shaft position 119.

In certain embodiments, housing 205 may function as an insulator or heat block to retain thermal energy in chamber 230 provided by heating module 201. In addition, housing 205 may comprise openings 207 for receiving and coupling fiber-optic cables 161. Furthermore, housing 205 may comprise an opening 208 for receiving chamber 230 and tapered wall 221 (defining a generally conical shape) configured to engage side surface 270 of chamber 230.

In particular embodiments, moveable magnetically responsive component 220 can be held in the second position for approximately 3 seconds, and then moved back to the first position for approximately 3 seconds to mix the contents of chamber 230. In certain embodiments, this cycling of moveable magnetically responsive component 220 between the first and second positions can be repeated for approximately 90 seconds. In particular embodiments, the rotation of shaft 110 between the first shaft position and the second shaft position can be controlled by PCR control module 60 of PCR modular assembly 50.

In specific embodiments, chamber 230 may comprise biological reagents that are inherently unstable at ambient temperatures and are stabilized with sugars via lyophilization. Lyophilization of biological reagents results in generation of material with low moisture content (e.g., less than 5 percent) and the functionality of the lyophilized material is compromised if it is not stored dry. Continued stability of lyophilized material therefore requires methods to prevent moisture absorption which includes secondary containers, storage in dry humidity environment, etc. In certain examples, a layer of wax can be used to create a moisture barrier for the lyophilized material that improves the stability of lyophilized reagents.

In certain embodiments, lyophilized material can be stabilized with insulating layer 213, which allows for storage of sample extraction cassette at ambient conditions without special requirements for a low humidity environment. As previously mentioned, insulating layer 213 can also used as a vapor barrier during PCR to reduce or prevent evaporation. After PCR cycling, insulating layer 213 (e.g. wax) can also solidify and create a full or partial barrier to potential amplicon contamination. An amplicon can be difficult to eliminate if it contaminates a lab and the solid wax significantly reduces the chance of such an occurrence.

The mixing process described herein can assist in the inversion of insulating layer 213 that has not naturally inverted by disrupting the surface tension at the insulating layer-resuspension buffer interface. Moveable magnetically responsive component 220 can also disrupt the surface tension, allowing for air bubbles that may be caught in the resuspension buffer to be released and rise to the top. Furthermore, the magnetic mixing process described herein can be used to mix the resuspension buffer with the lyophilized cake and promote uniform distribution of components, as well as reduce a temperature gradient within chamber 230.

Figure 11:
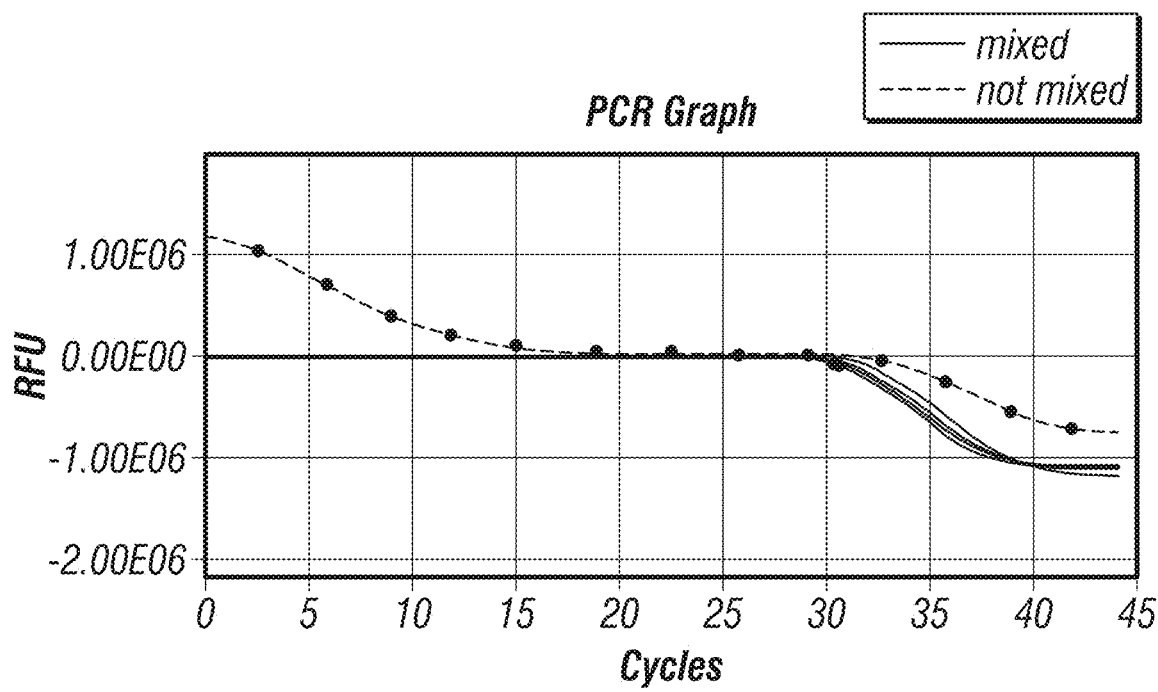
FIG. 11 is a graph of relative fluorescence units (RFU) detected during PCR plotted against PCR cycles performed by the embodiment of FIG. 1.
Figure 12:
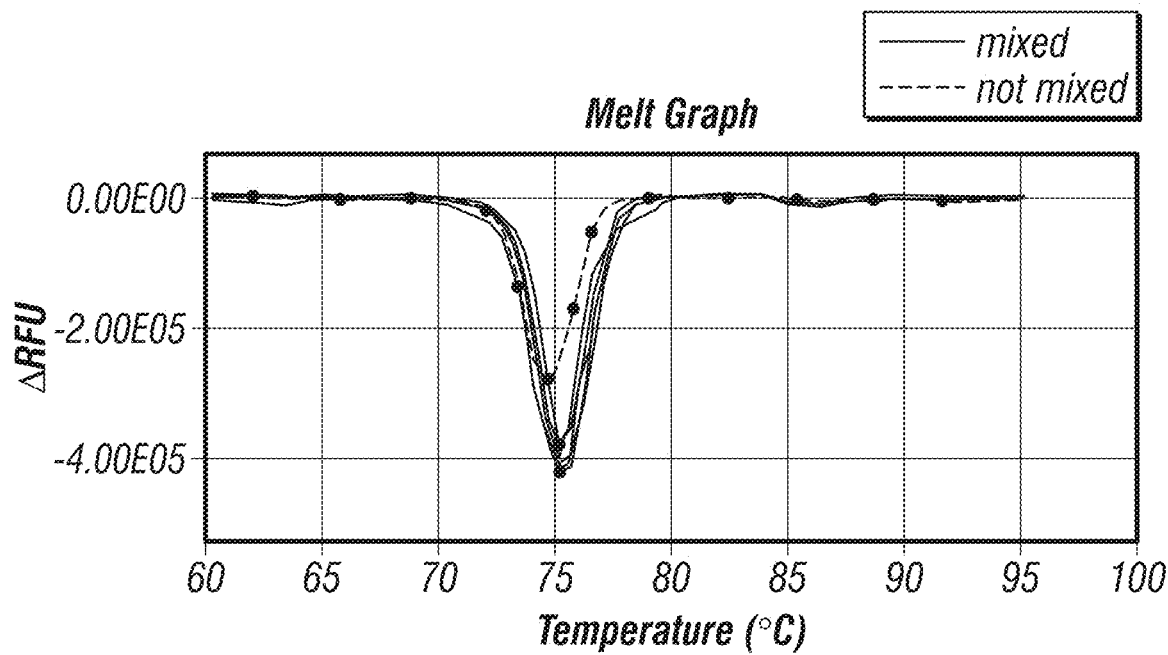
FIG. 12 is a graph of the delta relative fluorescence units (RFU) detected during melt plotted against temperature performed by the embodiment of FIG. 1.

Examples of the benefits of mixing contents of chamber 230 can be illustrated in FIGS. 11 and 12. In FIG. 11, the relative fluorescence units (RFU) detected during PCR are plotted against PCR cycles. FIG. 12 illustrates the delta in RFU plotted against temperature in a derivative melt curve. In FIGS. 11 and 12 the lighter/dotted line illustrates results from of contents that are not mixed in the PCR chamber, while the darker (non-dotted) lines illustrated results from contents that are mixed. FIG. 11 shows that the non-mixed results did not reach the desired baseline RFU value until approximately 18-20 cycles had been performed and there was a delay in shoulder between mixed and non-mixed. FIG. 12 shows the delta RFU is substantially reduced in the non-mixed results as compared to those of the mixed results.

Figure 13:
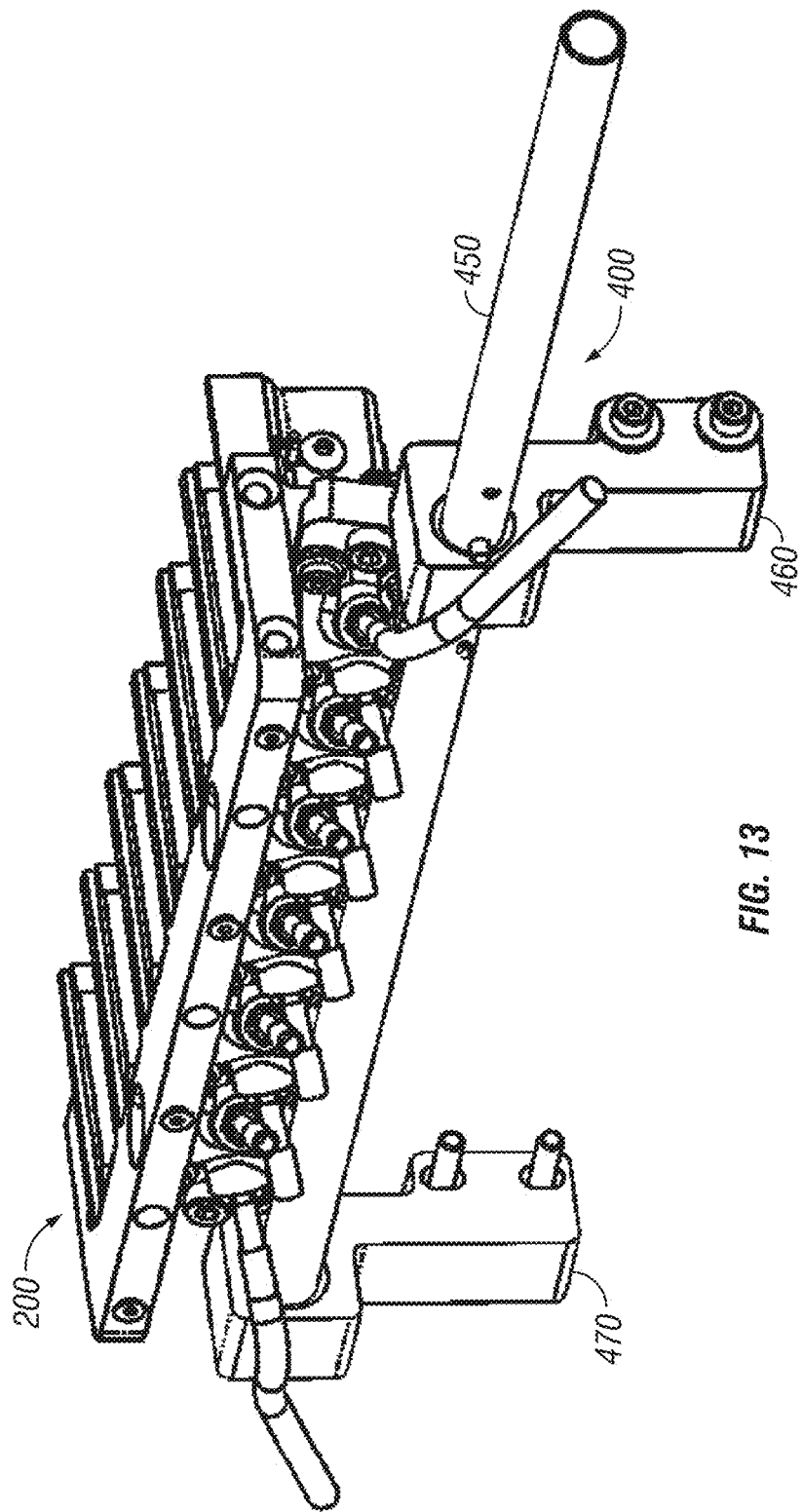
FIG. 13 is a perspective view of a partial magnetic actuation assembly and a (TEC) sub-assembly.
Figure 14:
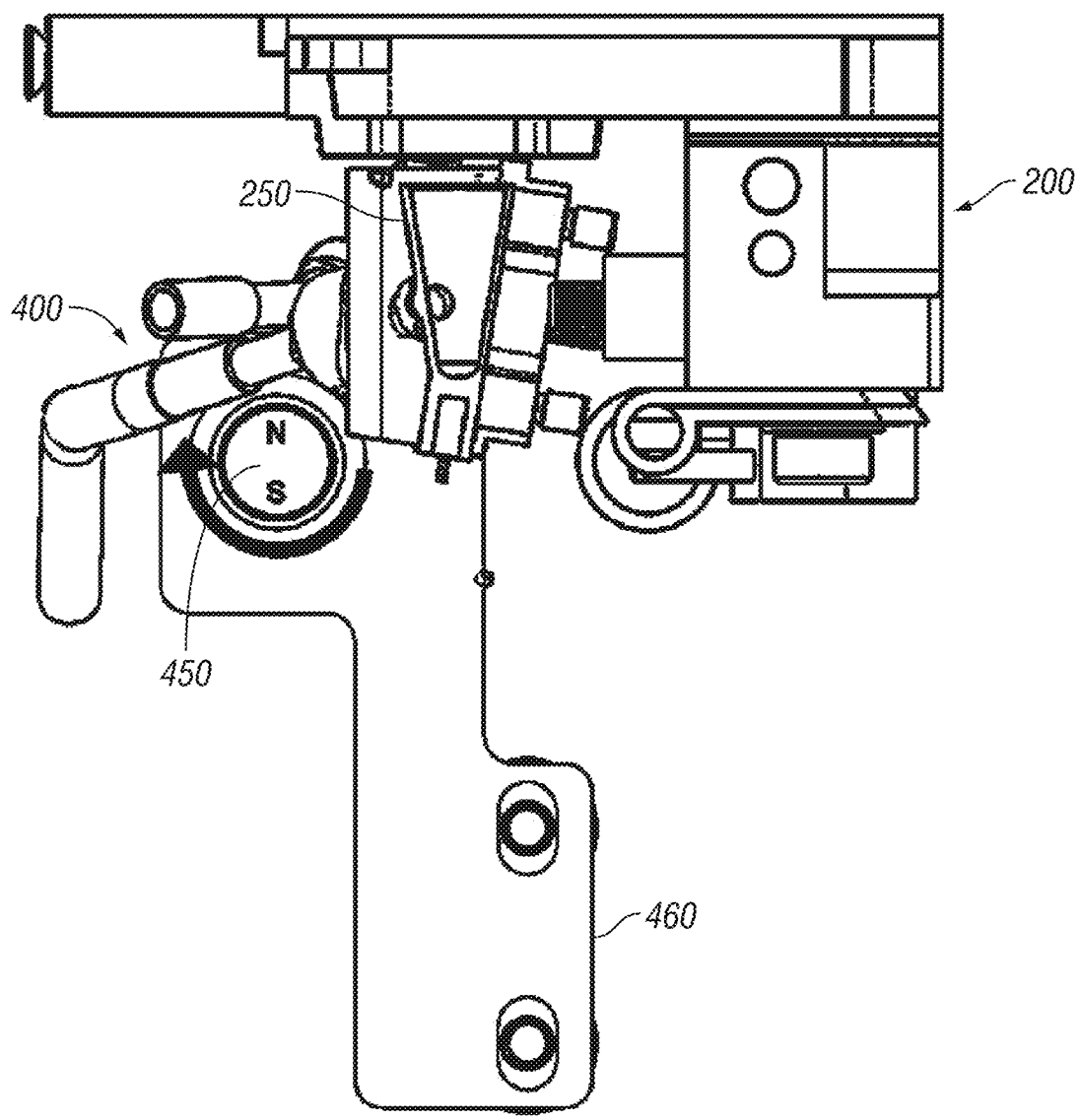
FIG. 14 is a partial section view of the embodiment of FIG. 13.

Other exemplary embodiments may utilize different components or configurations from those disclosed above. For example, certain exemplary embodiments may comprise a rotating magnetic rod rather than a plurality of magnets coupled to a rotating rod. Referring now to FIGS. 13-14, TEC 200 is coupled to a magnetic actuation assembly 400 that comprises a rotating magnetic rod 450 supported by brackets 460 and 470. As shown in the axial view of FIG. 14, magnetic rod 450 is radially magnetized such that the north pole (N) of the magnetic field extends from location on the circumference of the rod and the south pole (S) of the magnetic field extends from a location approximately 180 degrees circumferentially from the north pole. Accordingly, as magnetic rod 450 rotates along axis 413, the north and south poles N and S will be directed toward insert 250 and a PCR chamber (not shown) inserted into insert 250. Similar to previously described embodiments, the alternating magnetic field can direct movement of a moveable magnetically responsive component contained within a PCR chamber disposed within insert 250. Such movement can be used for multiple purposes, including for example, mixing components or reducing a temperature gradient.

Figure 15:
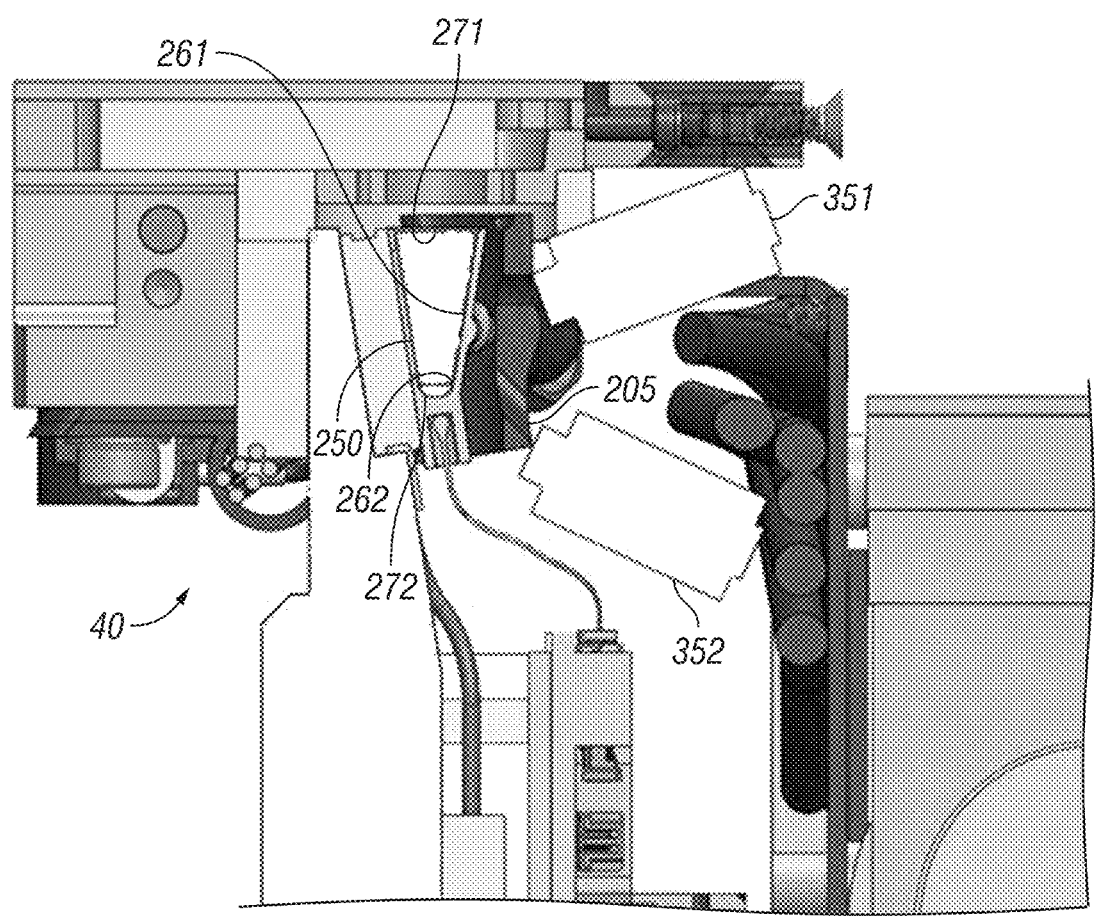
FIG. 15 is a partial section view of a PCR modular assembly comprising electromagnets.

In addition to the previously described embodiments, certain embodiments may utilize electromagnets to apply a magnetic force to the contents of a PCR chamber, including a moveable magnetically responsive component. Referring now to FIG. 15, a polymerase chain reaction (PCR) modular assembly 40 configured for nucleic acid amplification comprises a first electromagnet 351 and a second electromagnet 352. Similar to previous embodiments, this embodiment also comprises housing 205 and insert 250. For purposes of clarity, not all features of insert 250 are labeled in FIG. 15, but it is understood that insert 250 in FIG. 15 comprises features equivalent to those shown in FIGS. 7 and 8 (including for example, tapered side surface 270 having first end 271 that is larger and open, and second end 272 that is smaller and closed.)

In this embodiment, first electromagnet 351 is proximal to a first location 261 on insert 250 that is located between first end 271 and second end 272. Second electromagnet 352 is proximal to a second location 262 that is proximal to second end 272 of insert 250. First and second electromagnets 351 and 352 are configured to alternatingly and respectively apply a magnetic force to first and second locations 261 and 262 on insert 250. For example, first electromagnet 351 can be energized to apply a magnetic force to first location 261 while second electromagnet 352 is not energized to exert a magnetic force. Subsequently, second electromagnet 352 can be energized to apply a magnetic force to second location 352 while first electromagnet 352 is not energized to apply a magnetic force. This pattern can be repeated such that magnetic forces are alternatingly applied to first and second locations 261 and 262.

Accordingly, as first and second electromagnets 351 and 352 are alternatingly energized to apply magnetic forces to first and second locations 261 and 262, respectively, the magnetic field will be varied within insert 250 and a PCR chamber (not shown) inserted into insert 250. Similar to previously described embodiments, the alternating magnetic field can direct movement of a moveable magnetically responsive component contained within a PCR chamber disposed within insert 250. Such movement can be used for multiple purposes, including for example, to mix components or reduce a temperature within the insert or a chamber disposed within the insert.

Figure 16:
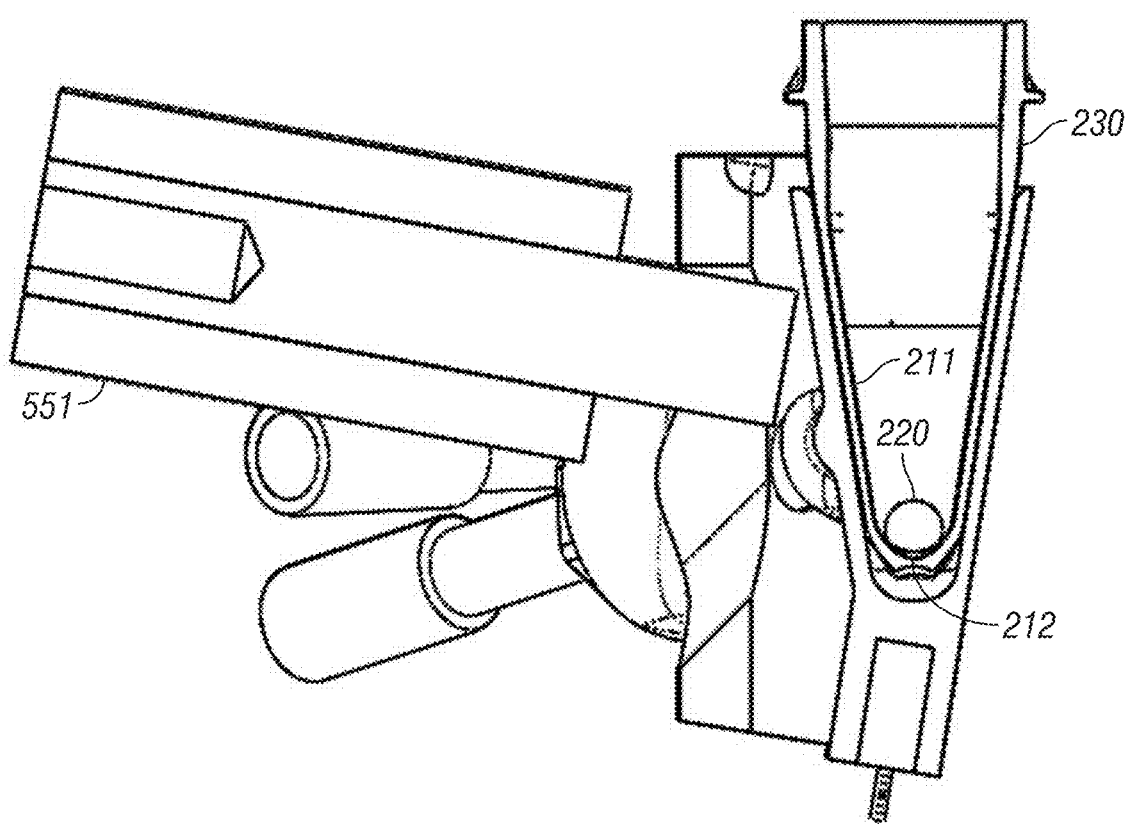
FIG. 16 is a partial section view of a PCR modular assembly comprising a single electromagnet.

Referring now to FIG. 16, another exemplary embodiment comprises a single electromagnet 551. This embodiment is similar to the embodiment described in FIG. 15, but allows the force of gravity to direct magnetically responsive component 220 to bottom surface 212 of chamber 230 (instead of a magnetic force applied by a second electromagnet). In this embodiment, electromagnet 551 can be energized to apply a magnetic force and direct magnetically responsive component 220 to side surface 211 of chamber 230. Electromagnet 551 can then be de-energized to reduce or eliminate the magnetic force applied to magnetically responsive component 220, allowing magnetically responsive component 220 to fall to bottom surface 212 of chamber 230. Electromagnet 551 can be alternatingly energized and de-energized to move the ball from a first location (e.g. side surface 211) to a second location (e.g. bottom surface 212). Such movement can be used, for example, to mix components or reduce a temperature within the insert or a chamber disposed within the insert.

Still other embodiments may comprise a different configuration of electromagnets. For example, certain embodiments may comprise two electromagnets at the same level, but wired in opposite polarity so that the magnetic flux jumps the gap between the electromagnets (similar to the spark in a spark plug). Other embodiments may comprise electromagnets that alternate polarity along an array of adjacent PCR chambers, for the effect of concentrating flux in the zone of the PCR chamber. Certain embodiments may comprise electromagnets with various back iron configurations to control the shape of the magnetic flux field.

It should be understood that the present devices and methods are not intended to be limited to the particular forms disclosed. Rather, they are to cover all modifications, equivalents, and alternatives falling within the scope of the claims. For example, in certain embodiments different configurations of magnets and or moveable magnetically responsive components may be used. In addition, other embodiments may use different time periods for holding shaft and moveable magnetically responsive components in the different positions.

The above specification and examples provide a complete description of the structure and use of an exemplary embodiment. Although certain embodiments have been described above with a certain degree of particularity, or with reference to one or more individual embodiments, those skilled in the art could make numerous alterations to the disclosed embodiments without departing from the scope of this invention. As such, the illustrative embodiment of the present devices is not intended to be limited to the particular forms disclosed. Rather, they include all modifications and alternatives falling within the scope of the claims, and embodiments other than the one shown may include some or all of the features of the depicted embodiment. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not to be interpreted as including means-plus- or step-plus-function limitations, unless such a limitation is explicitly recited in a given claim using the phrase (s) "means for" or "step for," respectively.

REFERENCES

The following references are incorporated herein by reference:
U.S. Pat. No. 5,352,036
U.S. Pat. No. 6,176,609
U.S. Pat. No. 6,357,907
U.S. Pat. No. 5,578,201
U.S. Pat. No. 8,048,375
U.S. Pat. No. 8,052,929
U.S. Pat. No. 8,550,694

We claim:

1. A method of mixing reagents, the method comprising: obtaining an apparatus comprising:
   a chamber containing a magnetically responsive component and reagents;
   a heating module;
   an insert configured to (i) receive the chamber, and (ii) conduct thermal energy from the heating module to the chamber; and
   a magnet coupled to a rotating shaft, where:
      the shaft is configured to move from a first shaft position to a second shaft position;
      in the first shaft position, the second end of the magnet is distal from the chamber; and
      in the second shaft position, the second end of the magnet is proximal to the chamber; and
   moving the shaft from a first position to a second position, wherein the magnetically responsive component is moved within the chamber from a first position to a second position, thereby mixing the reagents.

2. The method of claim 1 wherein the chamber comprises a bottom surface and a side surface, and wherein the magnetically responsive component contacts the bottom surface in the first position and wherein the magnetically responsive component contacts the side surface in the second position.

3. The method of claim 1 wherein:
   the magnetically responsive component is moved from the first position to the second position and held in the second position for approximately 3 seconds; and
   the magnetically responsive component is moved from the second position to the first position and held in the first position for approximately 3 seconds.

4. The method of claim 3 wherein the magnetically responsive component is cycled between the first and second positions for approximately 90 seconds.

5. The method of claim 1 wherein at least one of the reagents is provided in a lyophilized form.

6. The method of claim 1 wherein the side surface of the chamber is tapered and the bottom surface of the chamber is curved.

7. The method of claim 6 wherein:
the bottom surface is curved with a first radius;
the moveable magnetically responsive component is a spherical ball with a second radius; and
the first radius is greater than the second radius.

8. The method of claim 1, comprising moving the magnetically responsive component prior to beginning a polymerase chain reaction.

9. The method of claim 1, comprising moving the magnetically responsive component during at least a portion of a polymerase chain reaction.

10. The method of claim 9, wherein movement of the magnetically responsive component occurs during a temperature ramping phase.

11. The method of claim 9, wherein movement of the magnetically responsive component from the first position to the second position reduces a temperature gradient in the chamber.

12. The method of claim 1, comprising moving the magnetically responsive component prior to and during a polymerase chain reaction.

13. The method of claim 1, comprising moving the magnetically responsive component prior to beginning a reverse transcription reaction.

14. The method of claim 1, comprising moving the magnetically responsive component during at least a portion of a reverse transcription reaction.

15. The method of claim 1, comprising moving the magnetically responsive component prior to and during a polymerase chain reaction.

16. A method of mixing reagents, the method comprising:
obtaining an apparatus comprising:
a chamber containing a magnetically responsive component and reagents; and
a magnet coupled to a rotating shaft, where:
the shaft is configured to move from a first shaft position to a second shaft position;
in the first shaft position, the second end of the magnet is distal from the chamber; and
in the second shaft position, the second end of the magnet is proximal to the chamber; and
moving the shaft from a first position to a second position, wherein the magnetically responsive component is moved within the chamber from a first position to a second position, thereby mixing the reagents, wherein movement of the magnetically responsive component from the first position to the second position inverts a wax lyophilized layer in the chamber.

17. The method of claim 1 wherein the magnetically responsive component is a sphere.

18. The method of claim 17 wherein the sphere has a diameter of approximately 0.0625 inches.

19. The method of claim 1 wherein the magnetically responsive component is a disk or a sphere having a first diameter, and wherein a distance from first position to the second position of the magnetically responsive component is between two and five times the first diameter.

20. The method of claim 1 wherein the reagents are polymerase chain reaction (PCR) reagents.

* * * * *